United States Patent
Kim et al.

(10) Patent No.: US 11,071,706 B2
(45) Date of Patent: Jul. 27, 2021

(54) COSMETIC COMPOSITION CONTAINING, AS ACTIVE INGREDIENT, ALBUMIN, HYALURONIC ACID OR COLLAGEN IN CELL CULTURE MEDIUM

(71) Applicant: BIOCOZ GLOBAL KOREA CORP., Seoul (KR)

(72) Inventors: Chan Wha Kim, Seoul (KR); Young Joon Kim, Tenafly, NJ (US)

(73) Assignee: BIOCOZ GLOBAL KOREA CORP., Seoul (KR)

( * ) Notice: Subject to any disclaimer, the term of this patent is extended or adjusted under 35 U.S.C. 154(b) by 256 days.

(21) Appl. No.: 16/089,510

(22) PCT Filed: Mar. 31, 2017

(86) PCT No.: PCT/KR2017/003589
§ 371 (c)(1),
(2) Date: Sep. 28, 2018

(87) PCT Pub. No.: WO2017/171497
PCT Pub. Date: Oct. 5, 2017

(65) Prior Publication Data
US 2020/0297613 A1 Sep. 24, 2020

Related U.S. Application Data

(60) Provisional application No. 62/316,948, filed on Apr. 1, 2016.

(51) Int. Cl.
| | | |
|---|---|---|
| *A61K 8/65* | (2006.01) | |
| *A61P 27/02* | (2006.01) | |
| *A61P 17/00* | (2006.01) | |
| *A61K 8/19* | (2006.01) | |
| *A61K 8/36* | (2006.01) | |
| *A61K 8/64* | (2006.01) | |
| *A61K 8/67* | (2006.01) | |
| *A61K 8/73* | (2006.01) | |
| *A61K 38/38* | (2006.01) | |
| *A61K 38/39* | (2006.01) | |
| *A61K 47/02* | (2006.01) | |
| *A61K 47/12* | (2006.01) | |
| *A61K 47/22* | (2006.01) | |
| *A61K 47/26* | (2006.01) | |
| *A61Q 19/00* | (2006.01) | |
| *A61Q 19/08* | (2006.01) | |

(52) U.S. Cl.
CPC .................. *A61K 8/65* (2013.01); *A61K 8/19* (2013.01); *A61K 8/36* (2013.01); *A61K 8/64* (2013.01); *A61K 8/673* (2013.01); *A61K 8/675* (2013.01); *A61K 8/735* (2013.01); *A61K 38/385* (2013.01); *A61K 38/39* (2013.01); *A61K 47/02* (2013.01); *A61K 47/12* (2013.01); *A61K 47/22* (2013.01); *A61K 47/26* (2013.01); *A61P 17/00* (2018.01); *A61P 27/02* (2018.01); *A61Q 19/005* (2013.01); *A61Q 19/08* (2013.01)

(58) Field of Classification Search
CPC .......... A61K 8/64; A61K 8/65; A61K 31/728; A61K 38/38; A61K 38/385; A61K 38/39; A61K 47/02; A61K 47/12; A61K 47/22; A61K 47/26; A61K 8/19; A61K 8/36; A61K 8/673; A61K 8/675; A61K 8/73; A61K 8/735; A61P 17/00; A61P 27/02; A61Q 19/00; A61Q 19/005; A61Q 19/08
See application file for complete search history.

(56) References Cited

U.S. PATENT DOCUMENTS

| | | | |
|---|---|---|---|
| 8,518,422 B2 | 8/2013 | Monks et al. | |
| 9,610,463 B2* | 4/2017 | Gohla | A61P 17/02 |
| 10,801,009 B2* | 10/2020 | Kim | A61P 17/00 |
| 2005/0226853 A1 | 10/2005 | Conrad et al. | |
| 2009/0202654 A1* | 8/2009 | Nixon | A61P 17/02 |
| | | | 424/574 |
| 2016/0074519 A1* | 3/2016 | Khabarov | A61K 31/198 |
| | | | 514/249 |

FOREIGN PATENT DOCUMENTS

| | | | |
|---|---|---|---|
| KR | 10-2011-0025530 A | 3/2011 | |
| KR | 10-2012-0089433 A | 8/2012 | |
| KR | 10-2013-0061950 A | 6/2013 | |
| KR | 10-2014-0103759 A | 8/2014 | |
| KR | 10-2016-0072090 A | 6/2016 | |
| WO | 00/69449 A2 | 11/2000 | |
| WO | 02/098365 A2 | 12/2002 | |
| WO | 2004/103333 A1 | 12/2004 | |
| WO | 2007/070850 A2 | 6/2007 | |

OTHER PUBLICATIONS

KR20120089433A translation machine translation from patents. google.com from KR to EN, 16 pages. (Year: 2012).*
KR20130061950A, Korean to English Machine translation access from patents.google.com, 17 pages. (Year: 2013).*
International Searching Authority, International Search Report of PCT/KR2017/003589 dated Jul. 11, 2017 [PCT/ISA/210].

* cited by examiner

*Primary Examiner* — Marcela M Cordero Garcia
(74) *Attorney, Agent, or Firm* — Sughrue Mion, PLLC

(57) ABSTRACT

The present invention relates to a cosmetic or pharmaceutical composition containing a cell culture medium and, as an active ingredient, albumin, hyaluronic acid or collagen. The composition according to the present invention can be useful as a cosmetic or pharmaceutical composition for alleviating, preventing or treating skin wounds, skin diseases or skin conditions, by increasing the recovery capability of cells.

6 Claims, 7 Drawing Sheets

[Fig. 1]
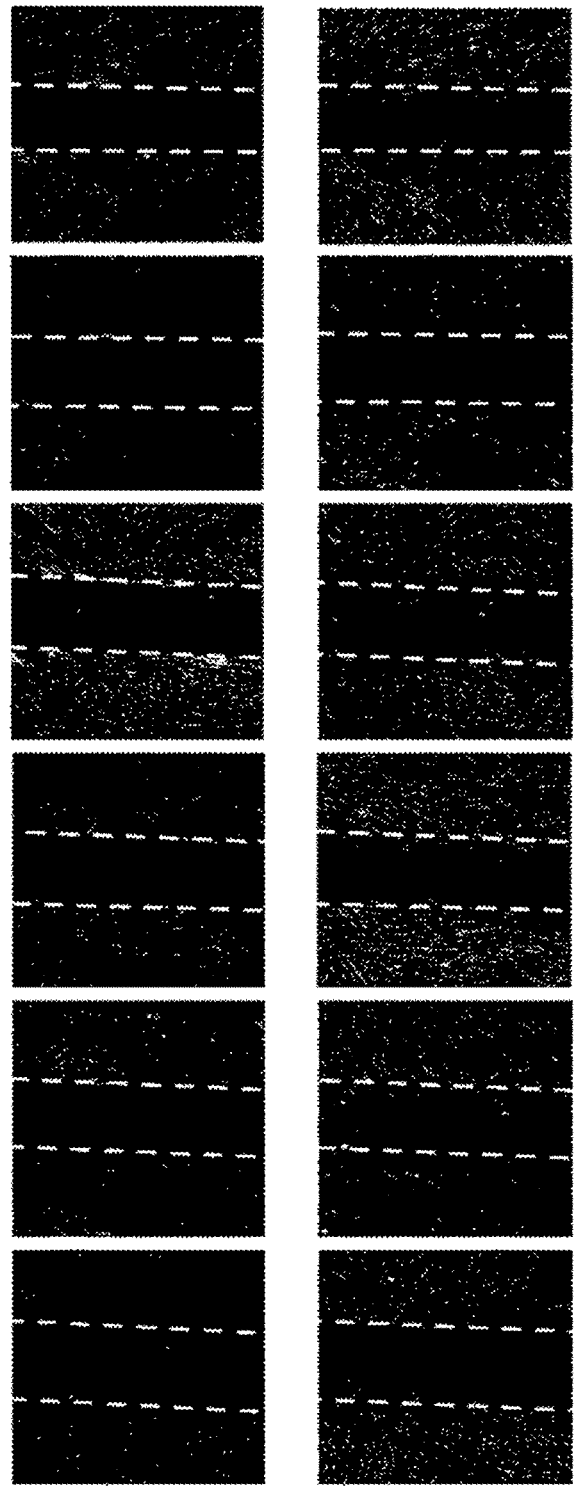

[Fig. 2]
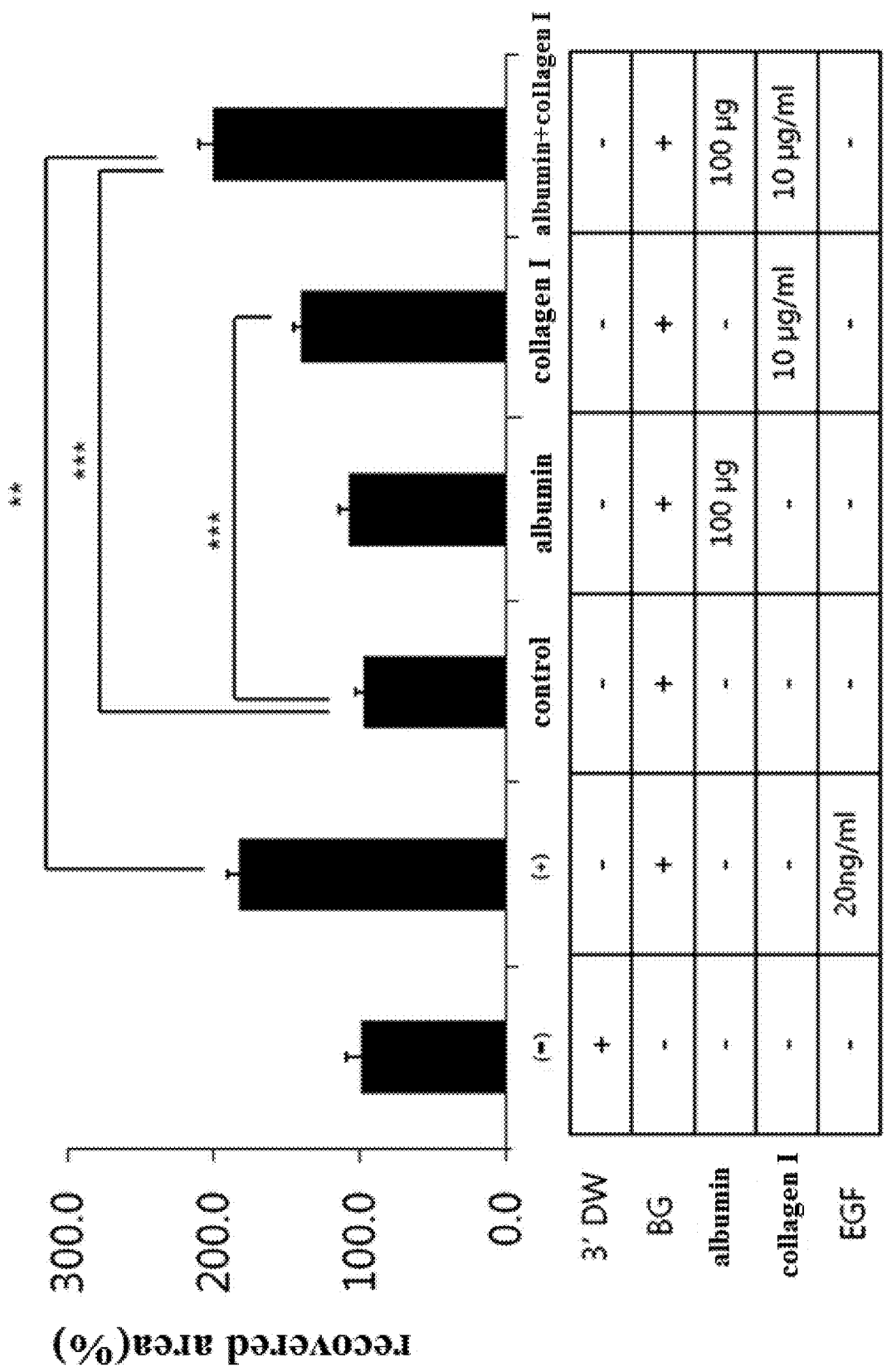

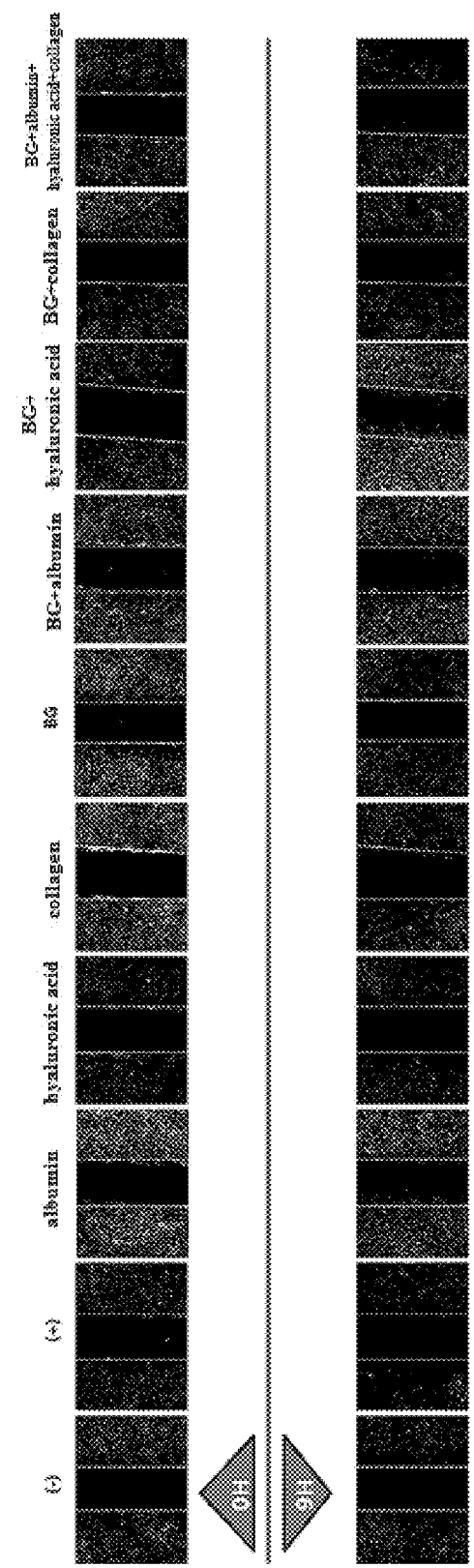
[Fig. 3]

[Fig. 4]
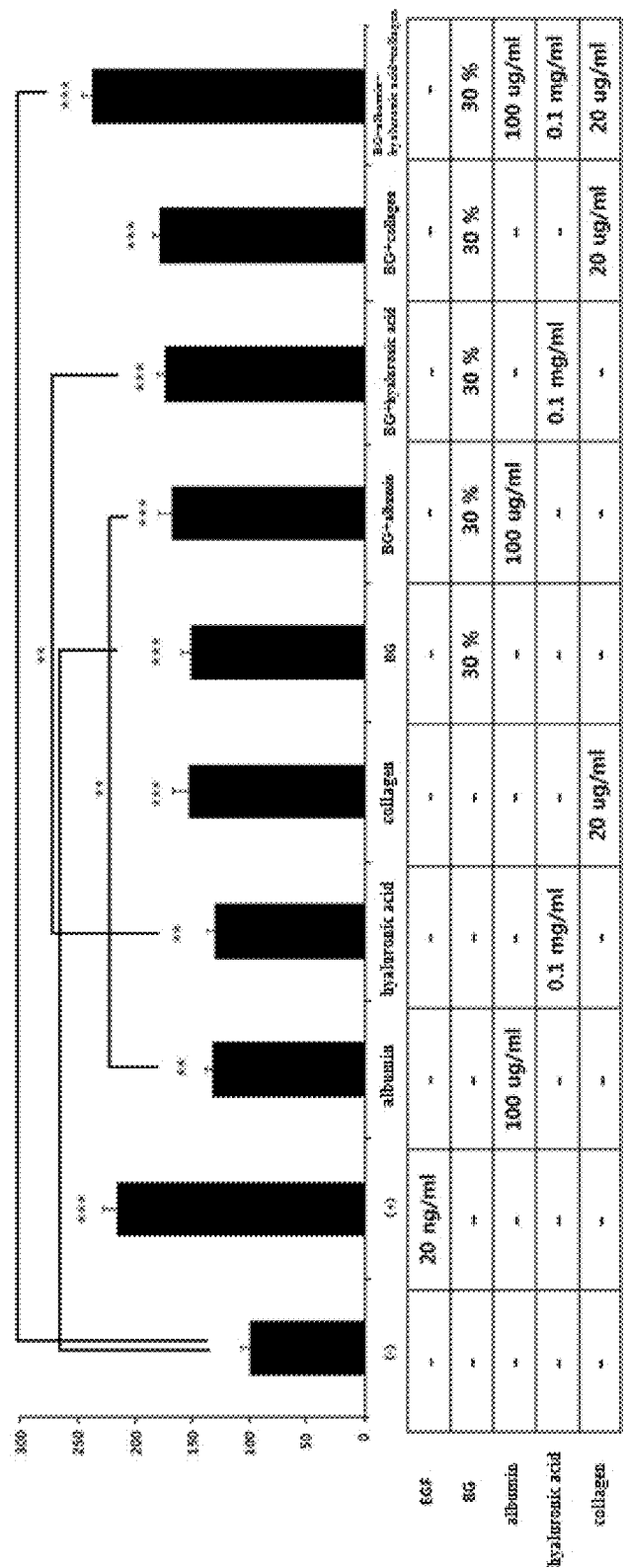

[Fig. 5]
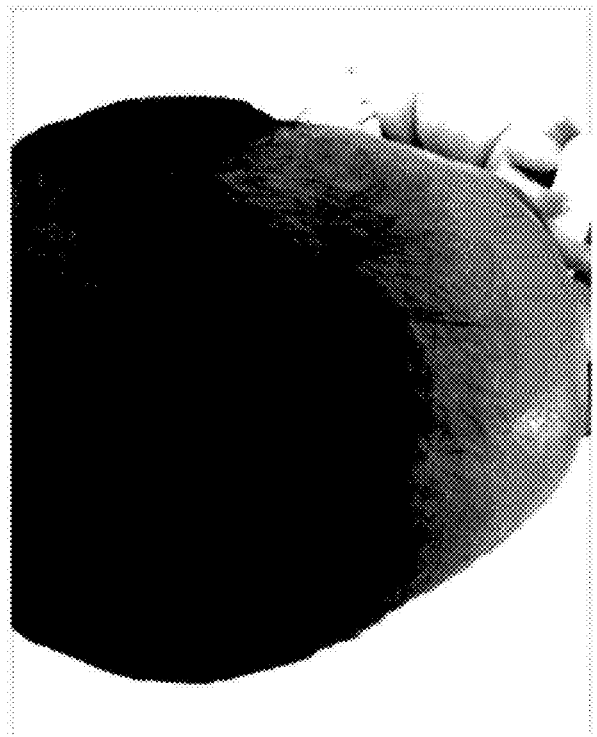
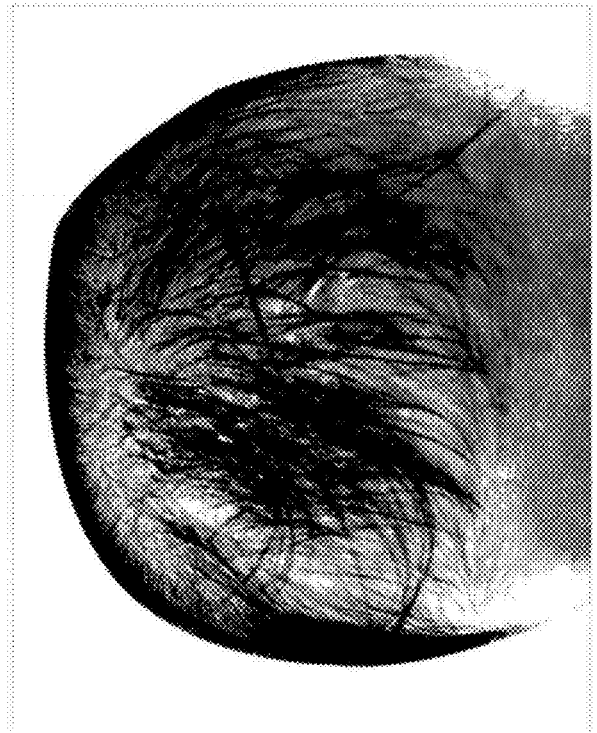

[Fig. 6]
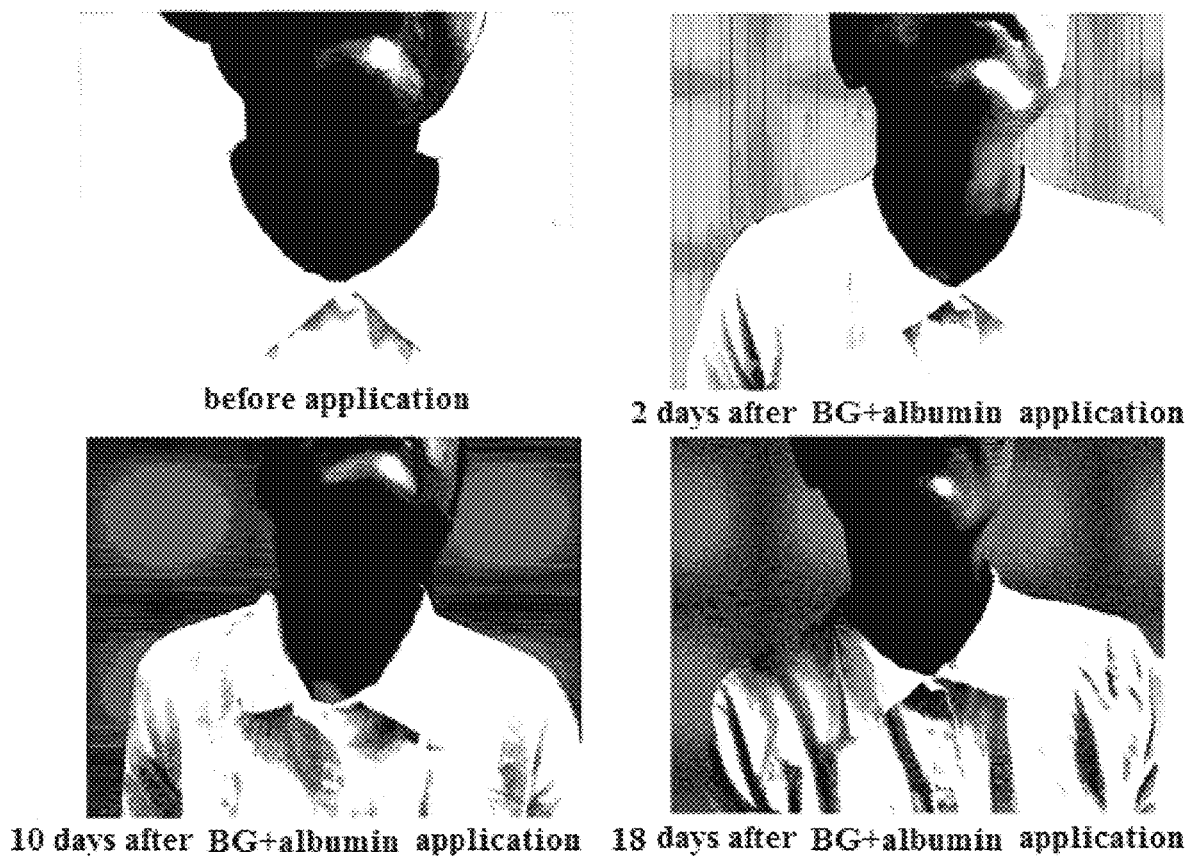

[Fig. 7]
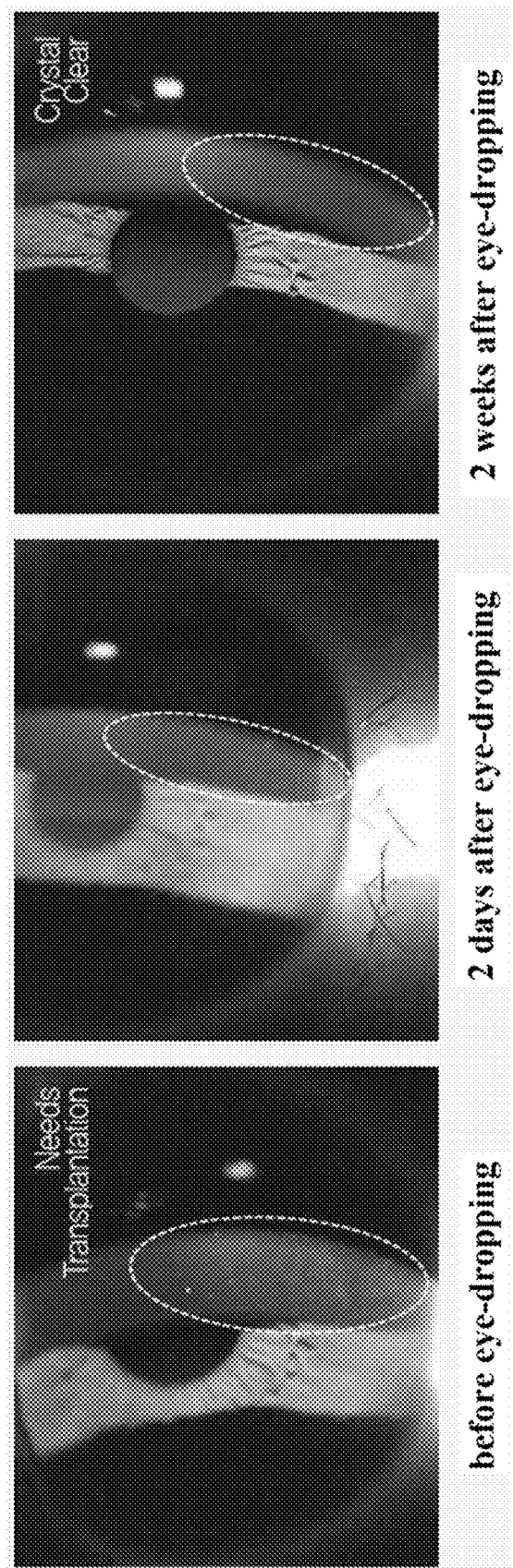

COSMETIC COMPOSITION CONTAINING, AS ACTIVE INGREDIENT, ALBUMIN, HYALURONIC ACID OR COLLAGEN IN CELL CULTURE MEDIUM

CROSS REFERENCE TO RELATED APPLICATIONS

This application is a National Stage of International Application No. PCT/KR2017/003589, filed Mar. 31, 2017, claiming priority based on U.S. Provisional Application No. 62/316,948, filed Apr. 1, 2016.

TECHNICAL FIELD

The present invention relates to a composition comprising albumin, hyaluronic acid, or collagen as an active ingredient in a cell culture medium.

The present invention also relates to a cosmetic composition comprising the above composition as an active ingredient, and a method for improving skin condition using the same.

The present invention also relates to a pharmaceutical composition for preventing or treating a skin disorder comprising the above composition as an active ingredient, and a method for preventing or treating a skin disorder using the same.

BACKGROUND ART

Allergic disorders are increasing significantly in various age groups due to changes in diet and residential life arising from intensification of industrialization and urbanization, and due to exposure to chemical or biological harmful substances arising from environmental pollution. A sensitive response of human body to a harmless external environment is manifested by a respiratory disorder such as asthma or rhinitis, or a skin disorder such as contact dermatitis, atopic dermatitis or the like.

Specifically, skin shows hypersensitive immune reactions by directly contacting with external allergens through air, food, or the like. Such allergic skin disorder is an inflammatory disorder arising from consistent exposure to external antigens such as food, bacteria, mites, climate and environmental factors, etc., and the manifestation of allergic reactions to various environmental factors differs from person to person depending on the genetic characteristics of each person.

Herein, allergy refers to a type of hypersensitivity reaction caused by immune imbalance, and is a reaction to a specific antigen called allergen. Allergic reactions are initiated by binding of allergens to mast cells or basophils in which histamine formed by decarboxylation of histidine by L-histidine decarboxylase is stored in granular forms, and then the cells are degranulated to secrete histamine and β-hexosaminidase.

Atopic dermatitis, a type of allergic disorder, is a chronic and recurrent skin disorder that mainly starts in infancy or childhood, and its prevalence is increasing worldwide. The cause of atopic dermatitis has not yet been clearly identified, but environmental factors, genetic predisposition, immunochemical reactions, skin barrier abnormalities, etc. are considered to be the major causes of the disease. It shows various symptoms, such as pruritus, dry skin, eczema, etc. The distribution of skin lesions and response patterns also vary depending on patient's ages.

Currently, drugs widely used for the treatment of atopic dermatitis generally include local steroids, local immunomodulators, systemic steroids, systemic immunosuppressants, antihistamines, etc. However, there are risks for various side effects caused by administration or oral intake of these drugs, and thus the development of an active ingredient which is safe and shows improving effect on dry skin and skin barrier abnormalities is required.

DISCLOSURE OF INVENTION

Technical Problem

Accordingly, the present inventors have endeavored to investigate and develop a substance for improving skin condition and treating skin disorders, and have found that a composition mixed with a specific substance increases wound healing ability of cells.

Solution to Problem

In accordance with one object of the present invention, there is provided a cosmetic composition comprising a cell culture medium, and any one of albumin, hyaluronic acid, and collagen as active ingredients.

In accordance with another object of the present invention, there is provided a method for improving skin condition, comprising applying the above cosmetic composition to the skin of a subject in need thereof.

In accordance with still another object of the present invention, there is provided a pharmaceutical composition comprising a cell culture medium, and any one of albumin, hyaluronic acid, and collagen as active ingredients.

In accordance with still another object of the present invention, there is provided a method for preventing or treating a skin disorder, comprising applying the above pharmaceutical composition to the skin of a subject in need thereof.

Advantageous Effects of Invention

A cosmetic or pharmaceutical composition comprising a cell culture medium, and any one of albumin, hyaluronic acid, and collagen as active ingredients increases recovery capability of cells, and thus it can be effectively used as a cosmetic or pharmaceutical composition for improving, preventing or treating skin wound from external damage, a skin disorder, or skin condition, and can be used a new cosmetic or therapeutic agent. Also, it can be utilized in skin ointments and functional cosmetics currently used, and thus it can be easily developed as an additive.

BRIEF DESCRIPTION OF DRAWINGS

FIG. 1 shows the wound healing effects of a composition comprising the prepared cell culture medium and compositions comprising albumin or collagen I on human skin fibroblasts.

FIG. 2 is a graph in which the wound healing effects of a composition comprising the prepared cell culture medium and compositions comprising albumin or collagen I on human skin fibroblasts were quantitated.

FIG. 3 shows the wound healing effects of a composition comprising the prepared cell culture medium and compositions comprising albumin, hyaluronic acid or collagen III on human skin fibroblasts.

FIG. 4 is a graph in which wound healing effects of a composition comprising the prepared cell culture medium and compositions comprising albumin, hyaluronic acid or collagen III on human skin fibroblasts were quantitated.

FIG. 5 shows the atopy-improving effect of a mixed composition of the cell culture medium and albumin.

FIG. 6 shows the atopy-improving effect of a mixed composition of the cell culture medium and albumin.

FIG. 7 shows the corneal regeneration effect of a mixed composition of the cell culture medium and albumin.

BEST MODE FOR CARRYING OUT THE INVENTION

In one aspect, the present invention provides a composition comprising a cell culture medium; and any one selected from the group consisting of albumin, hyaluronic acid, and collagen.

The term "cell culture medium" as used herein, contains the components required for cell growth and survival in vitro, or components that aid cell growth and survival. Specifically, the components may be vitamins, essential or nonessential amino acids, and trace elements. The medium may be a medium used for culturing cells, preferably eukaryotic cells, more preferably animal cells.

Known examples of the cell culture medium include DMEM/F-12 (Dulbecco's Modified Eagle's Medium/Nutrient Mixture F-12), DMEM, MEMα (Minimum Essential Mediuma), BME (Basal Medium Eagle), GMEM (Glasgow Minimum Essential Medium), RPMI-1640 Medium, but are not limited thereto.

In addition, the cell culture medium of the present invention is serum-free. The serum-free medium means a culture medium which is not supplemented with serum derived from an animal (for example, animal-derived serum) including a human. Animal-derived serum provides a universal nutrient for the growth of cells to be cultured, but it has problems in that it is difficult to analyze because it contains unidentified trace components, and it is difficult to establish a reproducible test and production process, and stability in a human body cannot be guaranteed. However, the cell culture medium according to the present invention is a serum-free medium, which ensures stability in a human body and enables the establishment of a reproducible test and production process.

In addition, the cell culture medium means a cell culture medium before culturing cells. Since it is a culture medium before culturing the cells, there is no change in the composition of the cell culture medium, and thus it can be used with a homogeneous quality commercially.

The cell culture medium according to the present invention is composed of an amino acid component, a vitamin component, an inorganic salt component, other component, and purified water wherein:

a) the amino acid component is at least one amino acid selected from the group consisting of glycine, L-alanine, L-valine, L-leucine, L-isoleucine, L-threonine, L-serine, L-cysteine, L-methionine, L-aspartic acid, L-asparagine, L-glutamic acid, L-glutamine, L-lysine, L-arginine, L-histidine, L-phenylalanine, L-tyrosine, L-tryptophan, L-proline, beta-alanine, gamma-aminobutyric acid, ornithine, citrulline, homoserine, triiodotyrosine, thyroxine and dioxyphenylalanine, or a combination thereof, and preferably, it is at least one selected from the group consisting of glycine, L-alanine, L-arginine, L-cysteine, L-glutamine, L-histidine, L-lysine, L-methionine, L-proline, L-serine, L-threonine and L-valine, or a combination thereof, b) the vitamin component is at least one vitamin selected from the group consisting biotin, calcium D-pantothenate, folic acid, niacinamide, pyridoxine hydrochloride, riboflavin, thiamine hydrochloride, vitamin B12, choline chloride, i-inositol and ascorbic acid, or a combination thereof, and preferably it is at least one selected from the group consisting of i-inositol, thiamine hydrochloride, niacinamide and pyridoxine hydrochloride, or a combination thereof, c) the inorganic salt component is at least one inorganic salt selected from the group consisting of calcium chloride ($CaCl_2$) (anhydrous), copper sulfate pentahydrate ($CuSO_4 \cdot 5H_2O$), ferric sulfate heptahydrate ($FeSO_4 \cdot 7H_2O$), magnesium chloride (anhydrous), magnesium sulfate ($MgSO_4$) (anhydrous), potassium chloride (KCl), sodium chloride (NaCl), disodium hydrogen phosphate ($Na_2HPO_4$), sodium hydrogen phosphate monohydrate ($NaH_2PO_4$—$H_2O$), zinc sulfate heptahydrate ($ZnSO_4 \cdot 7H_2O$), ferric nitrate nonahydrate ($Fe(NO_3)_3 \cdot 9H_2O$), and sodium bicarbonate ($NaHCO_3$), or a combination thereof, and preferably, it is at least one inorganic salt selected from the group consisting of sodium chloride (NaCl), sodium hydrogen carbonate ($NaHCO_3$), potassium chloride (KCl), calcium chloride ($CaCl_2$) (anhydrous) and sodium hydrogen phosphate monohydrate ($NaH_2PO_4$—$H_2O$) or a combination thereof, d) the other component is at least one selected from the group consisting of D-glucose (dextrose), sodium pyruvate, hyphoxanthin Na, thymidine, linoleic acid, lipoic acid, adenosine, cytidine, guanosine, uridine, 2'-deoxyadenosine, 2'-deoxycytidine HCl, 2'-deoxyguanosine, or a combination thereof, and preferably, it is sodium pyruvate, and e) the purified water is used to dissolve the above amino acids, vitamins, inorganic salts and other components, and may be water obtained by distillation of at least single distillation or by purification through a filter.

According to an embodiment of the present invention, the cell culture medium is preferably composed of glycine, L-alanine, L-arginine hydrochloride, L-cysteine hydrochloride-monohydrate, L-glutamine, L-histidine hydrochloride-monohydrate, L-lysine hydrochloride, L-methionine, L-proline, L-serine, L-threonine, L-valine, i-inositol, thiamine hydrochloride, niacinamide, pyridoxine hydrochloride, sodium chloride (NaCl), sodium hydrogen carbonate ($NaHCO_3$), potassium chloride (KCl), calcium chloride ($CaCl_2$) (anhydrous), sodium hydrogen phosphate monohydrate ($NaH_2PO_4$—$H_2O$), and sodium pyruvate The amino acid component is used for cell growth as a raw material for protein synthesis. The amino acid component may comprise 0.2 to 1.2 parts by weight of glycine, 0.08 to 0.3 part by weight of L-alanine, 2 to 7 parts by weight of L-arginine hydrochloride, 0.2 to 0.9 part by weight of L-cysteine hydrochloride-monohydrate, 10 to 18 parts by weight of L-glutamine, 0.8 to 2.0 parts by weight of L-histidine hydrochloride-monohydrate, 1.0 to 5.0 parts by weight of L-lysine hydrochloride, 0.2 to 1.2 parts by weight of L-methionine, 0.2 to 1.2 parts by weight of L-proline, 1.0 to 5.0 parts by weight of L-threonine, and 1.0 to 5.0 parts by weight of L-valine based on 1 part by weight of amino acid serine contained in a cell culture medium.

One specific example of the amino acid components and contents in the cell culture medium according to the present invention may be 0.5 to 1.0 part by weight of glycine, 0.1 to 0.2 part by weight of L-alanine, 5.0 to 6.0 parts by weight of L-arginine hydrochloride, 0.4 to 0.7 part by weight of L-cysteine hydrochloride monohydrate, 12 to 15 parts by weight of L-glutamine, 1.0 to 1.5 parts by weight of L-histidine hydrochloride-monohydrate, 2.0 to 4.0 parts by weight of L-lysine hydrochloride, 0.4 to 0.8 part by weight of L-methionine, 0.4 to 0.8 part by weight of L-proline, 1.5 to 2.5 parts by weight of L-threonine and 1.5 to 2.5 parts by weight of L-valine. By containing amino acid components according to the contents and ranges described above, it is possible to aid the growth and maintenance of cells and improve formulation stability of the formulation.

In the cell culture medium, the vitamin component plays a role of maintaining cell activity, and may comprise 0.2 to 0.9 part by weight of i-inositol, 0.04 to 0.8 part by weight of thiamine hydrochloride, 0.04 to 0.8 part by weight of niacinamide and 0.04 to 0.8 part by weight of pyridoxine hydrochloride, based on 1 part by weight of amino acid serine.

One specific example of the vitamin components and contents in the cell culture medium according to the present invention may be 0.4 to 0.7 part by weight of i-inositol, 0.06 to 0.2 part by weight of thiamine hydrochloride, 0.06 to 0.2 part by weight niacinamide and 0.06 to 0.2 part by weight of pyridoxine hydrochloride. By containing vitamin components according to the contents and ranges described above, it is possible to aid the maintenance of cell activity.

The inorganic salt component plays the role of controlling the expression of cell functions, and may comprise 50 to 200 parts by weight of sodium chloride (NaCl), 50 to 120 parts by weight of sodium hydrogen carbonate (NaHCO$_3$), 2.0 to 20 parts by weight of potassium chloride (KCl), 1.0 to 10 parts by weight of calcium chloride (CaCl$_2$) (anhydrous) and 0.5 to 5.0 parts by weight of sodium hydrogen phosphate monohydrate (NaH$_2$PO$_4$—H$_2$O), based on 1 part by weight of amino acid serine.

One specific example of the inorganic salt components and contents in the cell culture medium according to the present invention may be 100 to 150 parts by weight of sodium chloride (NaCl), 80 to 100 parts by weight of sodium hydrogen carbonate (NaHCO$_3$), 8 to 15 parts by weight of potassium chloride (KCl), 2.0 to 8.0 parts by weight of calcium chloride (CaCl$_2$)) (anhydrous) and 1.0 to 4.0 parts by weight of sodium hydrogen phosphate monohydrate (NaH$_2$PO$_4$—H$_2$O) based on 1 part by weight of amino acid serine.

The other component may include a component that maintains the pH of the cell culture medium and the like, and may comprise 0.5 to 5.0 parts by weight of sodium pyruvate based on 1 part by weight of amino acid serine.

One specific example of the other components and the content in the composition according to the present invention may be 1.0 to 4.0 parts by weight of sodium pyruvate based on 1 part by weight of amino acid serine. By containing the other components according to the contents and ranges described above, it is possible to aid the maintenance of the pH and thus improving the stability of the formulation.

The albumin constituting the composition of the present invention may be human serum albumin or bovine serum albumin.

The human serum albumin is serum albumin found in human blood, and is the most abundant protein present in human plasma. In the present invention, human serum albumin may specifically be recombinant human serum albumin. In addition, the bovine serum albumin is serum albumin found in cattle, and is often used as a protein concentration standard in experiments.

The albumin may be comprised at a concentration of 10 µg/ml, 50 µg/ml, 100 µg/ml, 200 µg/ml, 300 µg/ml, 500 µg/ml or 1000 µg/ml. Alternatively, the albumin may be comprised at a concentration of 10 to 1000 µg/ml, 50 to 500 µg/ml, or 100 to 250 µg/ml.

In addition, a hyaluronic acid constituting the composition of the present invention is a biosynthesized natural substance which exists in a large amount in the skin of an animal or the like, which is a hydrophilic substance, and plays a role of moisturization in the skin of an animal or the like.

The hyaluronic acid may be comprised at a concentration of 0.01 mg/ml, 0.1 mg/ml, 0.5 mg/ml, 1 mg/ml, 5 mg/ml or 10 mg/ml. The hyaluronic acid may be comprised at a concentration of 0.01 to 1 mg/ml, 0.05 to 0.5 mg/ml, or 0.01 to 0.1 mg/ml.

Meanwhile, as for the collagen constituting the composition according to the present invention, collagen I to collagen IV can be used, and in a specific example, collagen I and collagen III can be used. Most preferably, the collagen may be collagen III.

There are about 20 kinds of collagen in the human body. Collagen I is the most abundant collagen found in the human body, and it constitutes about 80 to 85% of skin, hair, nails, organs, bones and ligaments. The collagen III is the second abundant collagen in the human body. It constitutes about 10 to 15% of skin, bones, cartilages, tendons and other connective tissues, and is also known as placenta collagen.

Collagen may be comprised at a concentration of 1 µg/ml, 5 µg/ml, 10 µg/ml, 20 µg/ml, 50 µg/ml, 100 µg/ml, 150 µg/ml or 200 µg/ml in the composition. The collagen may be comprised at a concentration of 1 to 200 µg/ml, 2 to 100 µg/ml or 10 to 80 µg/ml.

Herein, collagen I may be comprised at a concentration of 1 to 100 µg/ml, 5 to 50 µg/ml, or 10 to 25 µg/ml in the composition, preferably 10 µg/ml. In addition, collagen III may be comprised at a concentration of 2 to 200 µg/ml, 10 to 120 µg/ml, and 20 to 70 µg/ml, preferably 20 µg/ml.

One embodiment of the present invention may be a composition comprising a cell culture medium and albumin. It may also be a composition comprising a cell culture medium and hyaluronic acid. It may also be a composition comprising a cell culture medium and collagen.

In addition, the composition may be a composition comprising a cell culture medium, albumin and collagen. The composition may also be a composition comprising a cell culture medium, albumin and hyaluronic acid. In addition, the composition may be a composition comprising a cell culture medium, collagen and hyaluronic acid.

The composition may also be a composition comprising a cell culture medium, albumin, collagen and hyaluronic acid.

As a result of the experiment, it was found that the recovery capability of human skin fibroblasts was further increased when the components were mixed and used for treatment as compared to single treatment of each component. Also, in an embodiment of the present invention, it was found that the composition comprising all of the cell culture medium, albumin and collagen I, or the cell culture medium, albumin, collagen III and hyaluronic acid showed superior wound healing effect as compared to a composition comprising a cell culture medium and EGF, which is known to have excellent skin improving effect (see FIG. 2 and FIG. 4).

The present invention also provides a cosmetic composition comprising the above composition. The composition has the effect of skin condition improvement. The "skin condition improvement" refers to an action of protecting the skin from reduction or loss of the function of skin cells, or improving skin condition, or preventing or treating a skin disorder, which is selected from the group consisting of inhibition of development of wrinkles, inhibition of skin aging, improvement of skin elasticity, skin regeneration, injury or wound healing, corneal regeneration, skin irritation alleviation, or a combination thereof. The skin disorder may be selected from the group consisting of atopic dermatitis, allergy, skin eczema, acne, psoriasis, pruritus, and a combination thereof.

The cosmetic composition according to the present invention can be used in preparing a cosmetic composition for improving skin condition.

The cosmetic composition may be formulated into a cosmetic formulation conventionally prepared in the art. The cosmetic composition may be formulated, for example, into solution, suspension, emulsion, paste, gel, cream, lotion, powder, soap, surfactant-containing cleansing, oil, powder foundation, emulsion foundation, wax foundation, spray, and the like, but the present invention is not limited thereto. More specifically, the cosmetic composition can be formulated into soft lotion, nutritional lotion, nutritional cream, massage cream, essence, eye cream, cleansing cream, cleansing foam, cleansing water, pack, spray or powder.

When the formulation of a cosmetic composition of the present invention is a paste, a cream or a gel, it may comprise a carrier component selected from the group consisting of animal oil, vegetable oil, wax, paraffin, starch, tragacanth, cellulose derivatives, polyethylene glycol, silicone, bentonite, silica, talc, zinc oxide, and a mixture thereof.

When the formulation of a cosmetic composition of the present invention is a solution or an emulsion, it may contain a carrier component selected from the group consisting of a solvent, a solvate, an emulsifier and a mixture thereof. Examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, sorbitan fatty acid ester, and a mixture thereof.

When the formulation of a cosmetic composition of the present invention is a suspension, it may comprise a carrier component selected from the group consisting of a liquid diluent (such as water, ethanol or propylene glycol), a suspension (such as ethoxylated isostearyl alcohol, polyoxyethylene sorbitol ester and polyoxyethylene sorbitan ester), microcrystalline cellulose, aluminum metahydroxide, bentonite, agar, tragacanth, and a mixture thereof.

The present invention provides a method for improving skin condition using the cosmetic composition.

The method for improving skin condition may comprise applying the cosmetic composition according to the present invention to the skin of a subject in need thereof. The subject may be a mammal, and specifically a human.

The step of applying the composition to the skin may comprise directly applying or spraying the cosmetic composition according to the present invention to the skin depending on its form. Herein, the application amount of the cosmetic composition and the number of daily usage can be appropriately adjusted according to the user's age, sex, purpose, severity of symptoms, etc. For example, an appropriate amount of the cosmetic composition can be applied to the skin one to six times a day.

The present invention also provides a pharmaceutical composition for preventing or treating a skin disorder comprising the composition according to the present invention as an active ingredient.

The pharmaceutical composition of the present invention has the same active ingredient as the above-mentioned cosmetic composition.

The skin disorder may be selected from the group consisting of atopic dermatitis, allergy, skin eczema, acne, psoriasis, pruritus, and a combination thereof.

The pharmaceutical composition may further comprise a pharmaceutically acceptable carrier.

The carrier may be comprised in an amount of about 1% to about 99.99% by weight, preferably about 90% to about 99.99% by weight, based on the total weight of the pharmaceutical composition of the present invention.

The pharmaceutical composition of the present invention can be applied to the skin.

The formulation of the pharmaceutical composition of the present invention may be in the form of an external preparation for skin such as an ointment, a solution, a cream, a spray, a patch, and the like.

The appropriate dosage of the pharmaceutical composition of the present invention is determined in consideration of various factors such as a formulation method, an administration method, patient's age, body weight, sex, pathological condition, food, administration time, administration route, excretion rate, sensitivity of responsiveness, etc., and thus the above dosage should not be construed as limiting the scope of the present invention in any aspect.

The present invention provides a method for preventing or treating a skin disorder using the above pharmaceutical composition.

The present invention also provides a use of the pharmaceutical composition in preparing a drug for preventing or treating a skin disorder.

The method for preventing or treating a skin disorder may comprise applying the pharmaceutical composition according to the present invention to the skin of a subject in need thereof. The subject to which the pharmaceutical composition can be applied may be a mammal, and specifically a human.

The step of applying the composition to the skin may comprise directly applying or spraying the cosmetic composition according to the present invention to the skin depending on its form. Herein, the application amount of the cosmetic composition and the number of daily usage can be appropriately adjusted according to the user's age, sex, purpose, severity of symptoms, etc. For example, an appropriate amount of the cosmetic composition can be applied to the skin one to six times a day.

MODE FOR THE INVENTION

Hereinafter, the present invention is explained in detail by Examples. The following Examples are intended to further illustrate the present invention without limiting its scope.

Preparation Example 1. Preparation of Cell Culture Medium

Each component described in Table 1 was thoroughly dissolved in ultrapure purified water and it was confirm that all the components were dissolved, followed by filtration through a 0.2 μm filter. All of the components listed in Table 1 below were purchased from Sigma-Aldrich, USA. A cell culture medium, which is a mixed composition containing the 22 components listed below, was prepared, and hereinafter referred to as BG.

TABLE 1

| Components | Concentration (g/L) |
| --- | --- |
| Glycine | 0.01875 |
| L-alanine | 0.00445 |
| L-arginine hydrochloride | 0.1475 |

TABLE 1-continued

| Components | Concentration (g/L) |
|---|---|
| L-cysteine hydrochloride-monohydrate-H$_2$O | 0.01756 |
| L-glutamine | 0.365 |
| L-histidine hydrochloride-monohydrate | 0.03148 |
| L-lysine hydrochloride | 0.09125 |
| L-methionine | 0.01724 |
| L-proline | 0.01725 |
| L-serine | 0.02625 |
| L-threonine | 0.05345 |
| L-valine | 0.05285 |
| i-inositol | 0.0126 |
| thiamine hydrochloride | 0.00217 |
| Niacinamide | 0.00202 |
| pyridoxine hydrochloride | 0.002 |
| sodium chloride (NaCl) | 3.49775 |
| sodium bicarbonate (NaHCO$_3$) | 2.438 |
| potassium chloride (KCl) | 0.3118 |
| calcium chloride (CaCl$_2$) (anhydrous) | 0.1166 |
| sodium phosphate monobasic monohydrate (NaH$_2$PO$_4$—H$_2$O) | 0.0625 |
| sodium pyruvate | 0.055 |

Examples 1 to 9. Preparation of Composition Comprising Cell Culture Medium, and Albumin, Collagen or Hyaluronic Acid Compositions were prepared by mixing albumin, collagen or hyaluronic acid with the BG prepared in Preparation Example 1, according to the contents shown in Table 2.

TABLE 2

| Example | Components |
|---|---|
| 1 | BG + albumin 100 μg/ml |
| 2 | BG + collagen I 10 μg/ml |
| 3 | BG + albumin 100 μg/ml + collagen I 10 μg/ml |
| 4 | BG + hyaluronic acid 0.1 mg/ml |
| 5 | BG + collagen III 20 μg/ml |
| 6 | BG + albumin 100 μg/ml + hyaluronic acid 0.1 mg/ml |
| 7 | BG + albumin 100 μg/ml + collagen III 20 μg/ml |
| 8 | BG + hyaluronic acid 0.1 mg/ml + collagen III 20 μg/ml |
| 9 | BG + albumin 100 μg/ml + hyaluronic acid 0.1 mg/ml + collagen III 20 μg/ml |

Examples 10 to 16. Preparation of Composition Comprising Cell Culture Medium, and Albumin, Collagen or Hyaluronic Acid Compositions were prepared by mixing MEMα (Sigma-Aldrich, USA) with albumin, collagen or hyaluronic acid according to the contents shown in Table 3.

TABLE 3

| Example | Components |
|---|---|
| 10 | MEMα + albumin 100 μg/ml |
| 11 | MEMα + collagen III 20 μg/ml |
| 12 | MEMα + hyaluronic acid 0.1 mg/ml |
| 13 | MEMα + hyaluronic acid 0.1 mg/ml + collagen III 20 μg/ml |
| 14 | MEMα + albumin 100 μg/ml + collagen III 20 μg/ml |
| 15 | MEMα + albumin 100 μg/ml + hyaluronic acid 0.1 mg/ml |
| 16 | MEMα + albumin 100 μg/ml + hyaluronic acid 0.1 mg/ml + collagen III 20 μg/ml |

Experimental Example 1. Evaluation of Recovery Capability of Cells

A human skin fibroblast cell line (Hs27) was cultured in a 37° C. thermo-hygrostat maintained at 5% CO$_2$ using the cell culture medium DMEM (1X) supplemented with 10% FBS (fetal bovine serum) and 1% P/S (Penicillin-Streptomycin). An ibidi Culture-insert was attached to a 6-well plate, in which human skin fibroblasts were cultured at $5.2 \times 10^4$ cells per insert well. After human skin fibroblasts cultured under the above condition for 24 hours, the cells were cultured again for 18 hours in serum-free DMEM (1X) culture solution for 18 hours to maintain the serum-free state until the present experiment. Then, the ibidi Culture-insert was removed.

1.1. Examination of Recovery Capability of Cells in Composition Containing BG, and Albumin or Collagen I The prepared cell culture solution was treated with BG (control group), a mixture composition of BG and 100 μg/ml of albumin (Example 1), a mixture composition of BG and 10 μg/ml of collagen I (Example 2), or a mixture composition of 100 μg/ml of albumin and 10 μg/ml of collagen I (Example 3).

9 hours after the treatment, the cells were photographed using a microscope, and the distances of the gaps caused by damage were measured using the TScratch program, and were compared with the control group. The results are shown in FIG. 1 and FIG. 2.

As shown in FIG. 1 and FIG. 2, it was found that the proliferation and migration of human skin fibroblasts were increased as compared to the control group when the cells were treated with the composition containing BG, and at least one of albumin or collagen I.

Specifically, when the cell culture solution containing BG was treated with albumin and collagen I in combination, the proliferation and migration of human skin fibroblasts were increased as compared to the cell culture solution with single treatment of albumin or collagen I, addressing that the mixed treatment was effective for wound healing. That is, it was found that the recovery capability of human skin fibroblasts was further increased when the cell culture solution containing BG was treated with albumin and collagen I in combination as compared to single treatment with albumin or collagen I.

1.2. Examination of Recovery Capability of Cells in Composition Containing Cell Culture Medium, and Albumin, Hyaluronic Acid, or Collagen III The prepared cell culture solution was treated with BG (control group), a mixture composition of BG and 100 μg/ml of albumin (Example 1), a mixture composition of BG and 0.1 mg/ml of hyaluronic acid (Example 4), a mixture composition of BG and 20 μg/ml of collagen III (Example 5), or a mixture composition of BG, 100 μg/ml of albumin, 0.1 mg/ml of hyaluronic acid and 20 μg/ml of collagen III (Example 9). In a control group, BG, 100 μg/ml of albumin, 0.1 mg/ml of hyaluronic acid, or 20 μg/ml of collagen III was added singly.

9 hours after the treatment, the cells were photographed using a microscope, and the distances of the gaps caused by damage were measured using the TScratch program, and the Experimental Examples were compared. The results are shown in FIG. 3 and FIG. 4.

As shown in FIG. 3 and FIG. 4, it was found that the proliferation and migration of human skin fibroblasts were further increased when the cells were treated with a combination of BG, albumin, hyaluronic acid, and collagen III after mixing the components, as compared to single treatment with BG, albumin, hyaluronic acid, or collagen III.

That is, it was found that the recovery capability of human skin fibroblasts was further increased when the cell culture solution was treated with a combination of BG, albumin, hyaluronic acid, and collagen III, as compared to single treatment with BG, albumin, hyaluronic acid, or collagen III 1.3. Examination of Recovery Capability of Cells in Composition Containing MEMα, and Albumin, Hyaluronic Acid or Collagen III Experiments were conducted by the same method as the Experimental Example 1.2, to examine the recovery capability of cells in Examples 10 to 16. As a result, it was found that the recovery capability of cells was superior when cell culture medium was treated with a combination of albumin, hyaluronic acid, and collagen III after mixing the components as compared to single treatment with each component. In addition, best recovery capability was observed when all of the three substances listed above were added in combination.

Experimental Example 2. Examination of Atopy Improvement Ability of Composition Comprising Cell Culture Medium and Albumin It was examined whether the composition comprising a cell culture medium prepared in Preparation Example 1 and 500 μg/ml of albumin was effective for atopy, which is a kind of skin disorder.

The composition comprising a cell culture medium and albumin was applied to the affected region (head) of a 6-month-old male atopic patient twice a day for 2 days. The result of the application was shown in FIG. 5. In addition, the composition comprising a cell culture medium and albumin was applied to the affected region (neck) of a 24-year-old female atopic patient twice a day for 10 days. The results were shown in FIG. 6.

As shown in FIG. 5 and FIG. 6, the wound induced by atopy on the head of the 6-month-old male child was significantly reduced after two days of application, and the wound induced by atopy on the neck of the 24-year-old female patient was significantly reduced after 10 days of application. This means that the mixed composition comprising a cell culture medium and albumin is effective for improving atopy.

Experimental Example 3. Evaluation of Corneal Regeneration Effect of Composition Comprising a Cell Culture Medium and Albumin It was examined whether the composition comprising the cell culture medium prepared in Preparation Example 1 (BG) and 100 μg/ml of albumin was effective for corneal erosion.

The composition comprising the cell culture medium and albumin was used for eye-dropping to the cornea (eyes) of a 32-year-old Korean female patient having refractory corneal erosion twice a day for 2 weeks. The result of the eye-dropping is shown in FIG. 7.

As shown in FIG. 7, it was found that the injured cornea of the patient with refractory corneal erosion was healed after 2 weeks of eye-dropping. This means that the mixed culture medium comprising the cell culture medium and albumin is effective for corneal regeneration.

The invention claimed is:

1. A method for improving skin condition of a subject, comprising administering a cosmetic composition to the subject,
   said composition comprising
   a cell culture medium; and
   one or more selected from the group consisting of albumin, hyaluronic acid, and collagen;
   wherein the cell culture medium comprises an amino acid component, a vitamin component, and an inorganic salt component, and
   wherein the amino acid component comprises 1 part by weight of serine, 0.2 to 1.2 parts by weight of glycine, 0.08 to 0.3 part by weight of L-alanine, 2 to 7 parts by weight of L-arginine hydrochloride, 0.2 to 0.9 part by weight of L-cysteine hydrochloride-monohydrate, 10 to 18 parts by weight of L-glutamine, 0.8 to 2.0 parts by weight of L-histidine hydrochloride-monohydrate, 1.0 to 5.0 parts by weight of L-lysine hydrochloride, 0.2 to 1.2 parts by weight of L-methionine, 0.2 to 1.2 parts by weight of L-proline, 1.0 to 5.0 parts by weight of L-threonine, and 1.0 to 5.0 parts by weight of L-valine, based on the 1 part by weight of serine.

2. The method of claim 1, comprising applying the cosmetic composition to a target skin of the subject.

3. The method of claim 2, wherein the subject is a mammal.

4. A method for preventing or treating a skin disorder in a subject in need thereof, comprising administering a pharmaceutical composition to the subject,
   said composition comprising
   a cell culture medium; and
   one or more selected from the group consisting of albumin, hyaluronic acid, and collagen;
   wherein the cell culture medium comprises an amino acid component, a vitamin component, and an inorganic salt component, and
   wherein the amino acid component comprises 1 part by weight of serine, 0.2 to 1.2 parts by weight of glycine, 0.08 to 0.3 part by weight of L-alanine, 2 to 7 parts by weight of L-arginine hydrochloride, 0.2 to 0.9 part by weight of L-cysteine hydrochloride-monohydrate, 10 to 18 parts by weight of L-glutamine, 0.8 to 2.0 parts by weight of L-histidine hydrochloride-monohydrate, 1.0 to 5.0 parts by weight of L-lysine hydrochloride, 0.2 to 1.2 parts by weight of L-methionine, 0.2 to 1.2 parts by weight of L-proline, 1.0 to 5.0 parts by weight of L-threonine, and 1.0 to 5.0 parts by weight of L-valine, based on the 1 part by weight of serine.

5. The method of claim 4, comprising applying the pharmaceutical composition to a target skin of the subject.

6. The method of claim 5, wherein the subject is a mammal.

* * * * *